(12) United States Patent
Peterson (10) Patent No.: US 11,078,460 B2
(45) Date of Patent: Aug. 3, 2021

(54) METHOD FOR INJECTABLE DELIVERY OF A THERAPEUTIC AGENT INTO A FISH EMBRYO

(71) Applicant: Tracy Shawn Peterson, Vancouver, WA (US)

(72) Inventor: Tracy Shawn Peterson, Vancouver, WA (US)

( * ) Notice: Subject to any disclaimer, the term of this patent is extended or adjusted under 35 U.S.C. 154(b) by 367 days.

(21) Appl. No.: 15/897,139

(22) Filed: Feb. 14, 2018

(65) Prior Publication Data

US 2018/0237742 A1    Aug. 23, 2018

Related U.S. Application Data

(60) Provisional application No. 62/460,758, filed on Feb. 18, 2017.

(51) Int. Cl.
| | | |
|---|---|---|
| *C12N 5/073* | (2010.01) | |
| *C12N 15/873* | (2010.01) | |
| *A01K 67/02* | (2006.01) | |
| *A01K 67/027* | (2006.01) | |
| *G01N 33/50* | (2006.01) | |

(52) U.S. Cl.
CPC ............ *C12N 5/0604* (2013.01); *A01K 67/02* (2013.01); *A01K 67/027* (2013.01); *C12N 15/873* (2013.01); *A01K 2207/20* (2013.01); *A01K 2227/40* (2013.01); *A61K 2123/00* (2013.01); *G01N 33/5005* (2013.01)

(58) Field of Classification Search
None
See application file for complete search history.

(56) References Cited

PUBLICATIONS

Vadstein (1997). Aquaculture 155: 401-417.
Almeida et al., (2009), "phage therapy and photodynamic therapy: Low environmental impact approaches to inactivate microorganisms in fish farming plants" Marine Drugs 7: 268-313.
Muktar et al., (2016), quoting Bowser PR (1999), Diseases of Fish. Cornell University, Ithica, New York, pp. 18-25.
Chen P.C.Y., Zhou s., Lu Z. et al (2015), Int. J. Control Autom. Syst. 13: 1233.
Spaink H.P., Cui C., Wiweger M.I. et al, Methods (2013) 62(3): 246-254.
Wang W, Liu C, Gelinas D, Ciruna B, Sun Y (2007) PLoS One 2(9): e862.
Hoffman et al. (1972), "Covalent Binding of Biomolecules to RAdiation-Grafted Hydrogels on Inert Polymer Surfaces," Trans. Am. Soc. Artif. Intern. Organs, 18, 10-18.
Monoclonal Antibodies in Fish Immunology: Identification, Ontogeny and Activity of T- and B-Lymphocytes, Scapigliati et al. Aquaculture 1999; 172:3-28.
Fish Immune System. A Crossroads between Innate and Adaptive Responses, Tort et al. Immunologia 2003; 22(3): 277-286.
The Astonishing Diversity of Ig Classes and B cell Repertoires in Teleost Fish, Fillatreau et al. Front Immunol Feb. 2013; 4(28):1-14.
Discovery of a Unique Ig Heavy-Chain Isotype (IgT) in Rainbow Trout: Implications for a Distinctive B cell Developmental Pathway in Teleost Fish, Hansen et al. PNAS May 10, 2005; 102(19): 6919-6924.
Recent Findings on the Structure and Function of Teleost IgT Zhang et al. Fish Shellfish Immunol Nov. 2011; 31(5): 627-634.
T cell Diversity and TcR Repertoires in Teleost Fish, Castro et al. Fish & Shellfish Immunology 2011; 31:644-654 I.
B Cells in Teleost Fish Act as Pivotal Initiating APCs in Priming Adaptive Immunity: An Evolutionary Perspective on the Origin of the B-1 Cell Subset and B7 Molecules, Zhu et al. J Immunol 2014; 192:2699-2714.
Muktar et al., (2016), quoting Bowser PR (1999), Diseases of Fish, Cornell University, Ithaca, New York, pp. 18-25.
Wang W, Liu X, Gelinas D, Ciruna B, Sun Y (2007) PLoS One 2(9): e862.

*Primary Examiner* — Christopher M Babic
*Assistant Examiner* — Kimberly A Aron
(74) *Attorney, Agent, or Firm* — David J. Kreher (57) ABSTRACT

Fish embryos may be successfully vaccinated or therapeutically treated if the therapeutic agent is injected into the yolk sac. Therapeutic agents may be directly injected or released from microspheres and enter the circulation and tissues. Injection into the yolk sac, combined with the use of carriers, allows for a continued, controlled release of therapeutic agents and processing of antigens. Fish vaccination or therapeutic treatment, selecting fish embryos post fertilization at the one-cell to eyed egg stage of development, and injecting the yolk sac with carriers associated with an antigen(s) or therapeutic agent(s), may be fully automated.

14 Claims, 12 Drawing Sheets

| 1 | 2 | 1 | 2 |

Anti-IgM　　　　　　　　　Anti-IgZ

Figure 4

Anti-IgM                                    Control Anti-IgM

Figure 12

METHOD FOR INJECTABLE DELIVERY OF A THERAPEUTIC AGENT INTO A FISH EMBRYO

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC

Not Applicable

AMENDED DESCRIPTION

Field of the Invention

The invention relates a method for the injectable delivery of a therapeutic agent into fish embryos, in particular, when the fish embryos are in the one-cell to the eyed egg stage of development.

AMENDED BACKGROUND OF THE INVENTION

All previous methods developed for vaccinating teleost fish have used teleost fish that are either in post-larval/juvenile, or in adult life stages. In fact, the accepted knowledge regarding the teleost immune system, is that fish could not be vaccinated at the embryo or larval stage due, not only to their small size, but also because they could not develop specific antibodies and hence, a protective immune response against pathogens until significantly later life stages, (see Vadstein (1997). Aquaculture 155; 401-417). Quoting Almeida et al., "Moreover, vaccination is not possible in the case of fish larvae, which generally are most susceptible to disease, because it is practically unfeasible to handle these small animals and also because it is believed that fish larvae do not have the ability to develop specific immunity." (Almeida et al., (2009). Phage therapy and photodynamic therapy: Low environmental impact approaches to inactivate microorganisms in fish farming plants. Marine Drugs 7; 268-313). "Yet, in other species, the major disease problems may appear in the larval or fry stages, before the animal is large enough to be vaccinated or have even developed a functional immune system." (See, Muktar et al., (2016), quoting Bowser P R (1999), Diseases of Fish. Cornell University, Ithaca, N.Y., pp: 18-25). However, the detection of antibodies in teleost fish can occur as early as two days post-fertilization.

Current therapeutic agent delivery methods such as injection into post-larval/juvenile or in adult fish, bath exposure and feed additives are not effective in preventing or treating disease in the early life stages of fish, when it is most economical and efficacious to administer. Existing methods result in wasted vaccine product(s) or therapeutic agent and often result in highly variable or suboptimal efficacy within the intended treatment population.

The most significant obstacle to effective prophylaxis or treatment of infectious diseases in early life stage fish is not the availability of vaccine agents, immunogenic potential, or processing of the vaccine agent, but a method of delivery. A convenient and cost-effective method to deliver therapeutic agents to fish is needed. The delivery of therapeutic agents is problematic due to inefficiency in administering the therapeutic agents and variable efficacy of vaccines. In addition, for vaccination to be optimally effective it must occur early in fish development before fish are exposed to pathogens.

Figure 8:
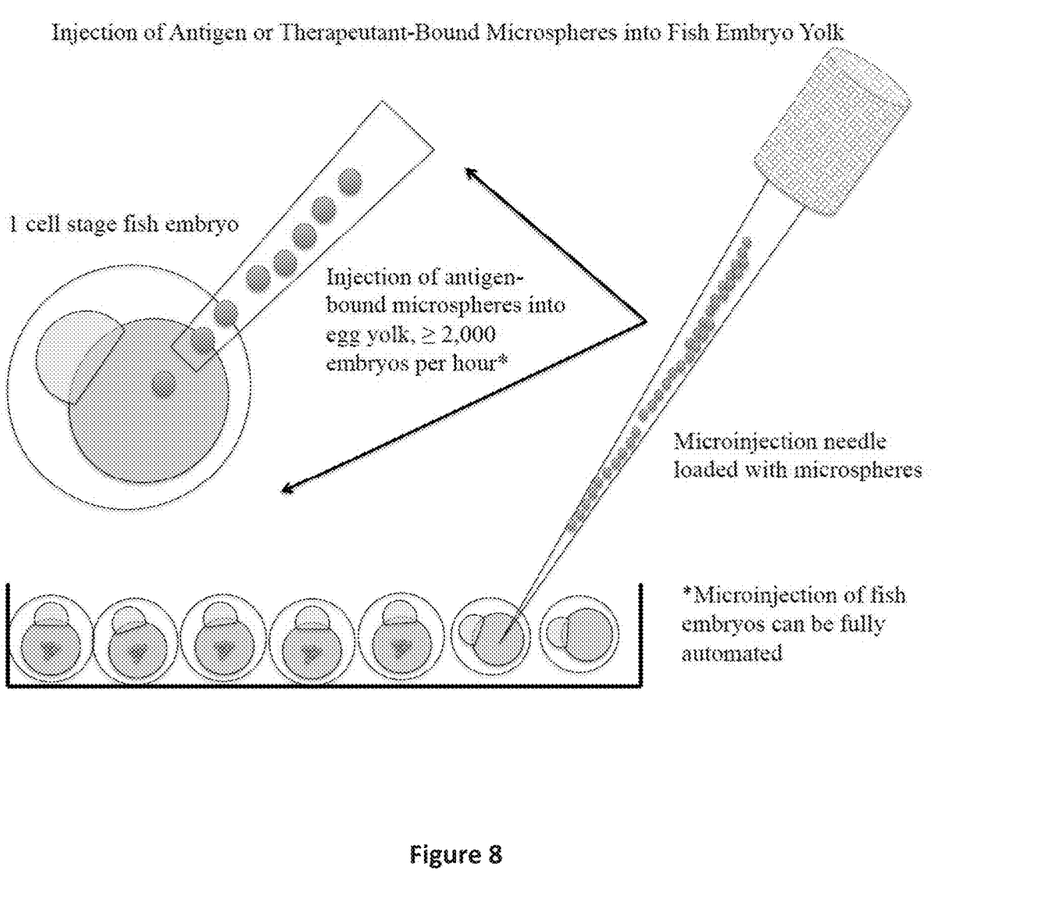
FIG. 8 demonstrates the general procedure of injection of therapeutic agent bound microspheres into the fish embryo yolk sac.
Figure 9:
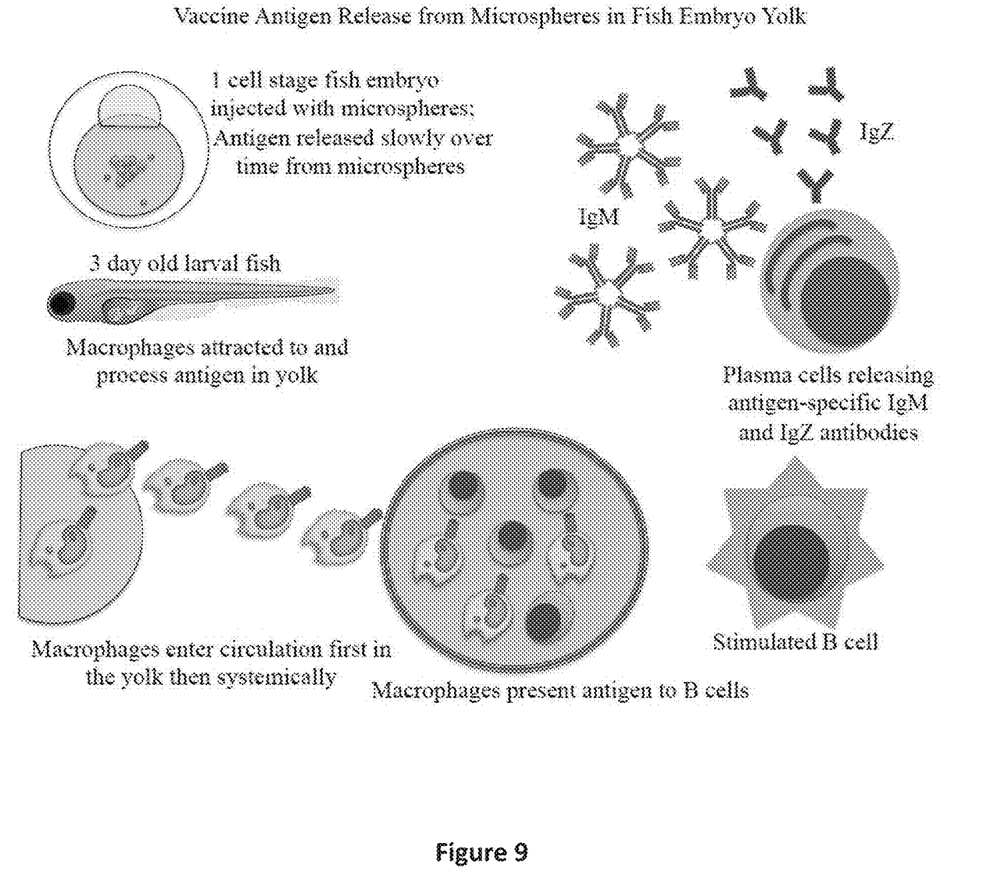
FIG. 9 illustrates how therapeutic agent bound microspheres, once injected into the fish embryo yolk sac, are used to vaccinate fish embryos.
Figure 10:
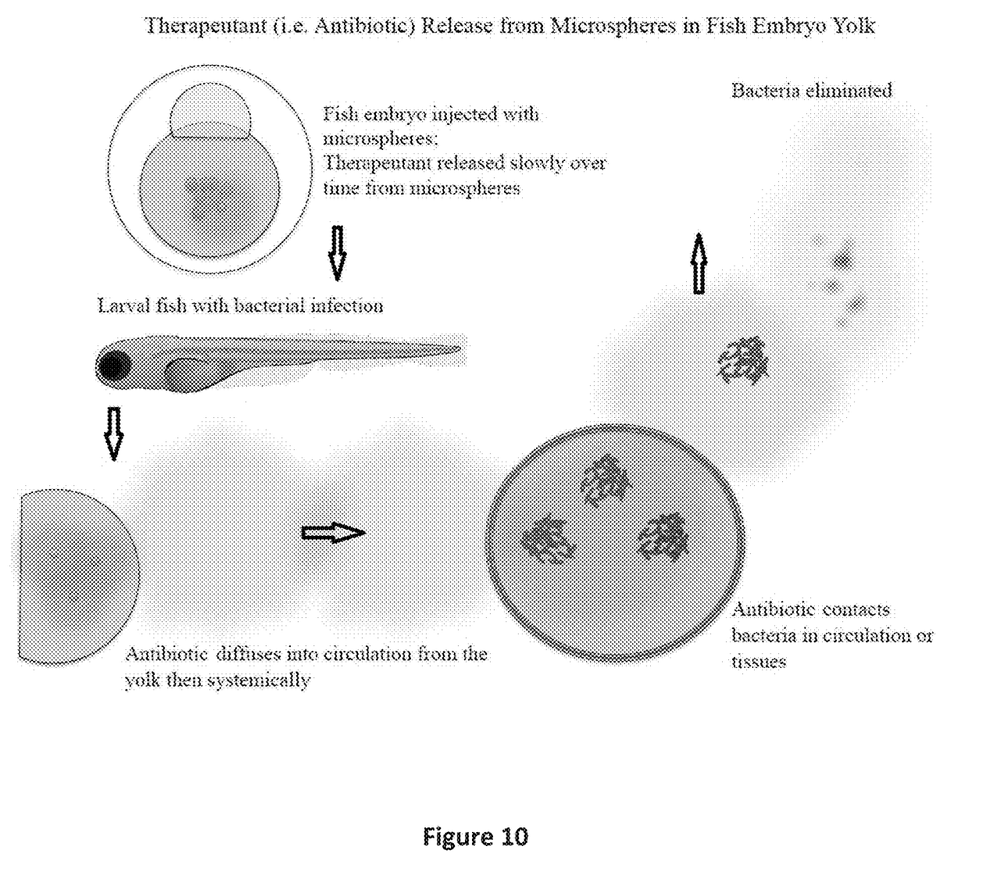
FIG. 10 illustrates how therapeutic agent bound microspheres, in this non-limiting example using an antibiotic, are used to treat or prevent infection in a larval fish.

At least partially based on the fact that antibodies can be detected in teleost fish as early as two days post-fertilization, the inventor reasoned that teleost fish embryos could be immunized with therapeutic agents by the injection of therapeutic agents into the embryo yolk sac. In addition, injection into the embryo yolk sac, combined with the use of carriers, would allow for a continued, controlled release and processing of therapeutic agents. For these reasons, the inventor developed a method of immunizing embryos post fertilization that are at the one-cell to eyed egg stage, by injecting the embryo yolk sac microspheres associated with a specific antigen (FIGS. 8 and 9).

Figure 1:
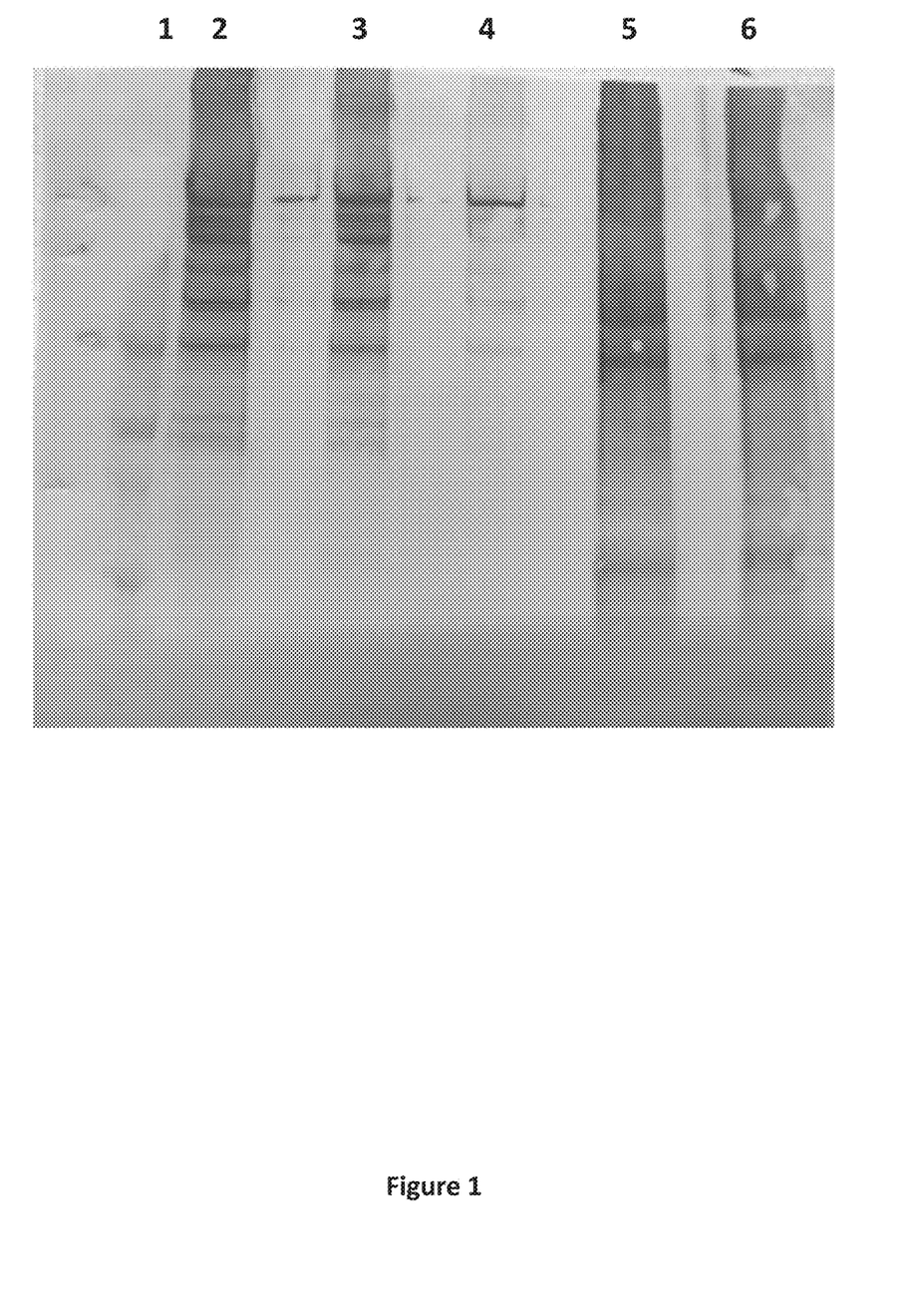
FIG. 1 illustrates Western blot analysis of Keyhole Limpet Hemocyanin (KLH) binding to Poly Lactic-co-Glycolic Acid (PLGA) microspheres, KLH was selected as representative antigen and its binding to PLGA microspheres was examined, samples of PLGA-COOH microspheres with covalently bound KLH were applied to SDS-PAGE, and separated material transferred to a PVDF membrane, to confirm the presence of KLH, membrane bound material was detected using a rabbit anti-KLH, followed by an anti-rabbit antibody coupled to horseradish peroxidase HRP, followed by 3,3'-Diaminobenzidine (DAB) for visualization, lane 1: molecular weight standards, lane 2: KLH 0.1 ug, lane 3: KLH 0.05 ug, lane 4, KLH 0.01 ug, lane 5: KLH PLGA bead prep #1, lane 6: KLH PLGA bead prep #2.
Figure 2:
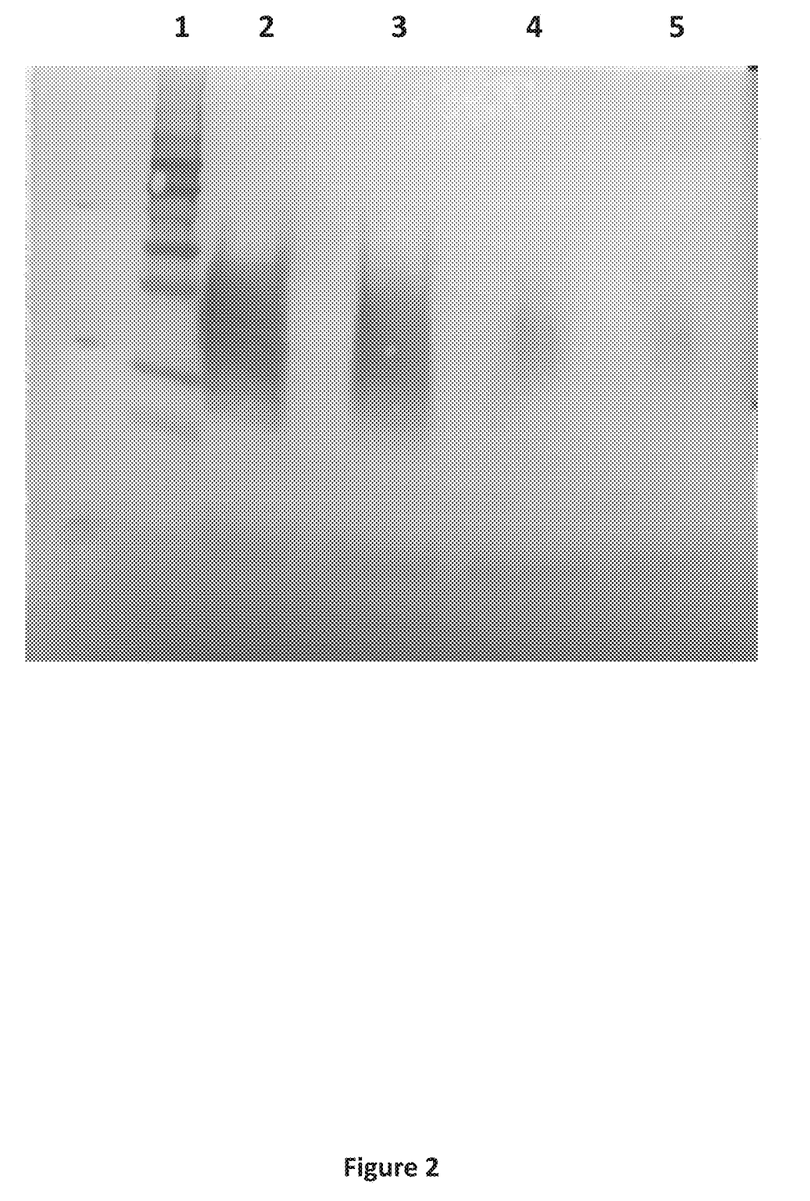
FIG. 2 illustrates a Western blot analysis of PLGA microspheres with bound *Mycobacterium marinum* (*M. marinum*) total protein, samples of PLGA microspheres with covalently bound *M. marinum* total protein extract were applied to SDS-PAGE and separated material transferred to a PVDF membrane, to confirm binding of *M. marinum* protein, an exemplary *M. marinum* protein, ESAT6, was identified using rabbit anti-ESAT6 followed by an anti-rabbit-HRP bound antibody and DAB for visualization, lane 1: molecular weight standards, lane 2: recombinant 25 ESAT6, lane 3: bead labeling elute, lane 4: *M. marinum* protein bead prep #1, lane 5: *M. marinum* protein bead prep #2.

After 1 month, 10 treated (injected with a carrier associated with KLH or *Mycobacterium marinum* protein antigen) and 10 control fish (injected with carrier with no antigen) were humanely euthanized and whole fish protein was isolated from two fish per tube by adding fish to 1 ml of G biosciences protein lysis buffer and protease inhibitors in a 2 ml tube containing sterile 11 mm diameter zirconia/silica beads and subjected to two minutes bead beating (Mini-Beadbeater, Biospec Products) to homogenize the samples and release total protein. All of the isolated protein within each group was pooled and used to detect antibodies specific to KLH or *Mycobacterium marinum* proteins. For detection of antibodies to KLH, 2 ug of KLH and BSA were run on a 3-8% tris acetate gel (except for 4 month experiment was run on 4-12% gel) for 40 min and transferred to PVDF membrane for 90 min. For detection of antibodies to *M. marinum* proteins, 40 ug of total protein and 2 ug of BSA were run on a 3-12% Tris Acetate gel for 30 min and transferred to PVDF membrane for 1 hour. Each membrane was blocked for 2 hours in 5% BSA/PBS at RT. Eighty ug of total pooled fish protein was added to 10 ml of 5% BSA/PBS and incubated with the membrane overnight at 4° C. The membrane was washed 3 times, 5 minutes each time, with 200 ml TPBS. Anti-IgM and Anti-IgZ antibodies (AnaSpec, Inc., AS_55789S) specific to zebrafish, were each labeled with HRP (Innova lightning link kit) and incubated with the membrane in solution to detect the presence of fish IgM or IgZ produced by the host fish against KLH or *M. marinum* proteins. After a 2-hour incubation, the membrane was washed 4× in 200 ul TPBS for 10 min each followed by addition of HRP detection reagent DAB. As evidenced by FIGS. 1 and 2, after approximately 5-15 min a band corresponding to a predicted molecular weight associated with KLH (between 290 and 500 kd on Western blot) or corresponding to multiple bands of *M. marinum* were detected.

Figure 3:
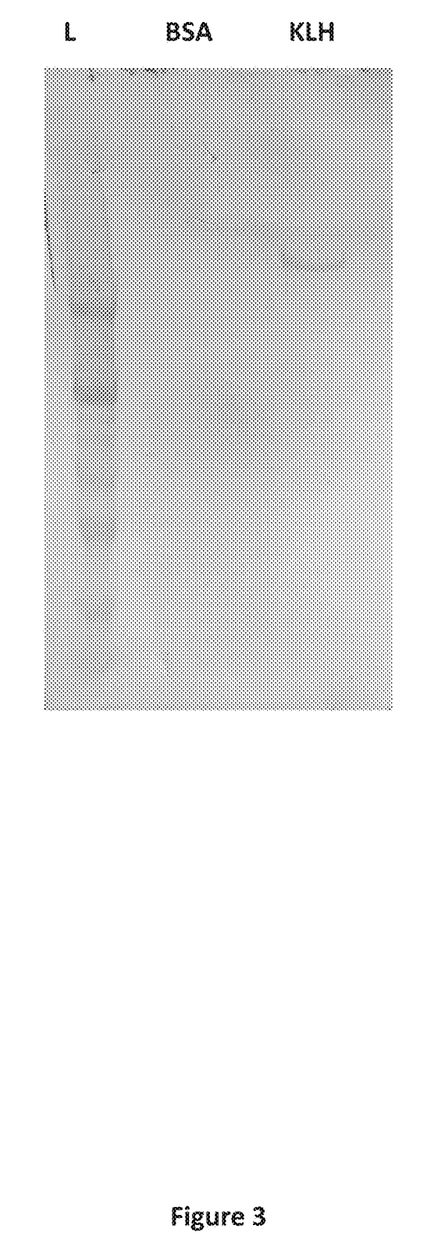
FIG. 3 illustrates the presence of IgM antibodies generated by zebrafish immunized against Keyhole Limpet Hemocyanin (KLH) 1 month post-immunization, KLH antigen and BSA, were separated by SDS-PAGE and transferred to a PVDF membrane, the detection of zebrafish antibodies was achieved using antibodies specific for zebrafish IgM (AnaSpec, Inc., AS_55789S) coupled with HRP, followed by DAB for visualization, lanes: L, Molecular weight markers, KLH; Keyhole Limpet Hemocyanin, BSA, bovine serum albumin control protein.
Figure 4:
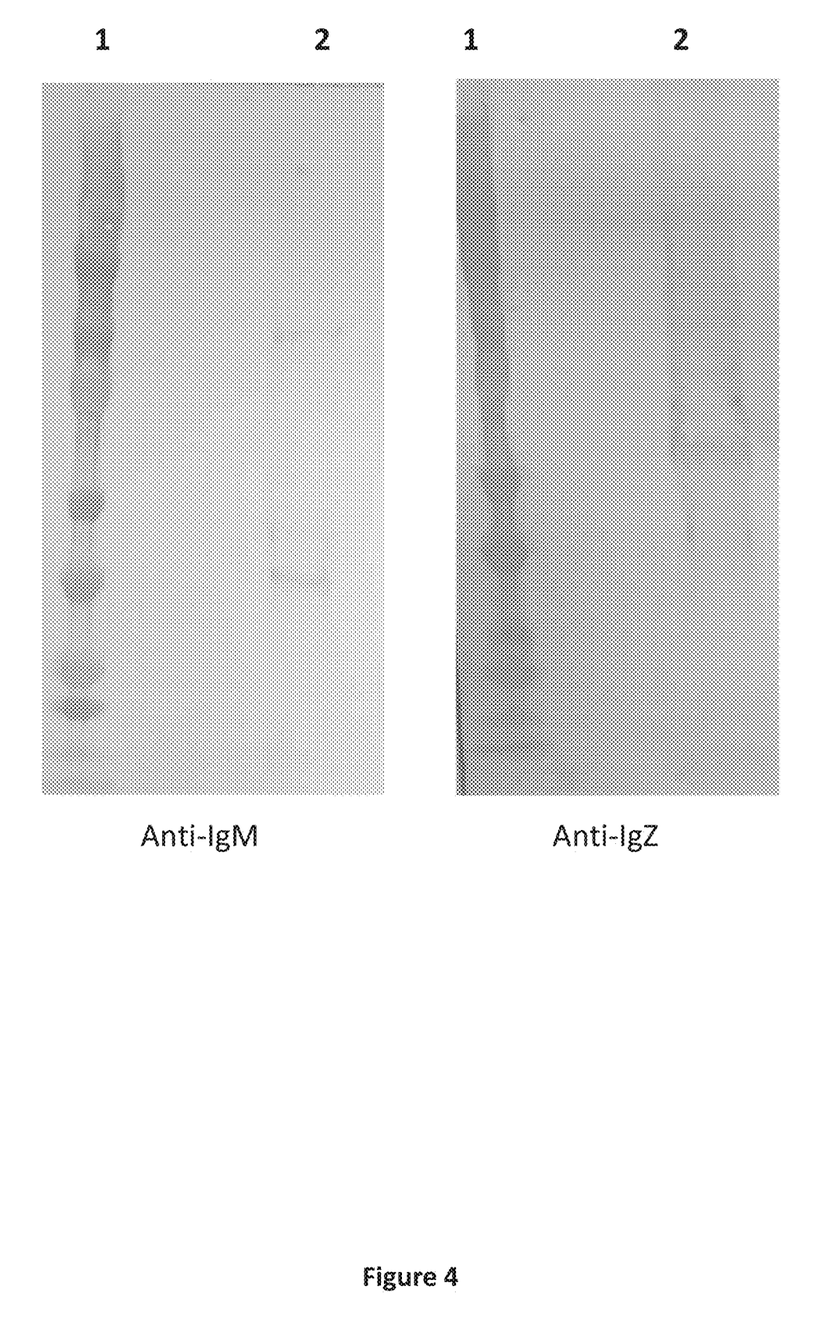
FIG. 4 illustrates the presence of IgM and IgZ antibodies generated by zebrafish immunized against *M. marinum*, 1 month post-immunization, *M. marinum* total protein antigens, were separated by SDS-PAGE and transferred to PVDF membrane, the PVDF membrane was incubated with pooled (10 fish) whole fish homogenate from both immunized and non-immunized fish, the detection of zebrafish antibodies was achieved using antibodies specific for zebrafish IgM and IgZ (AnaSpec, Inc., AS_55789S) coupled with HRP, followed by DAB for visualization, lanes: 1, molecular weight markers; lanes 2, whole fish homogenate from vaccinated zebrafish.
Figure 5:
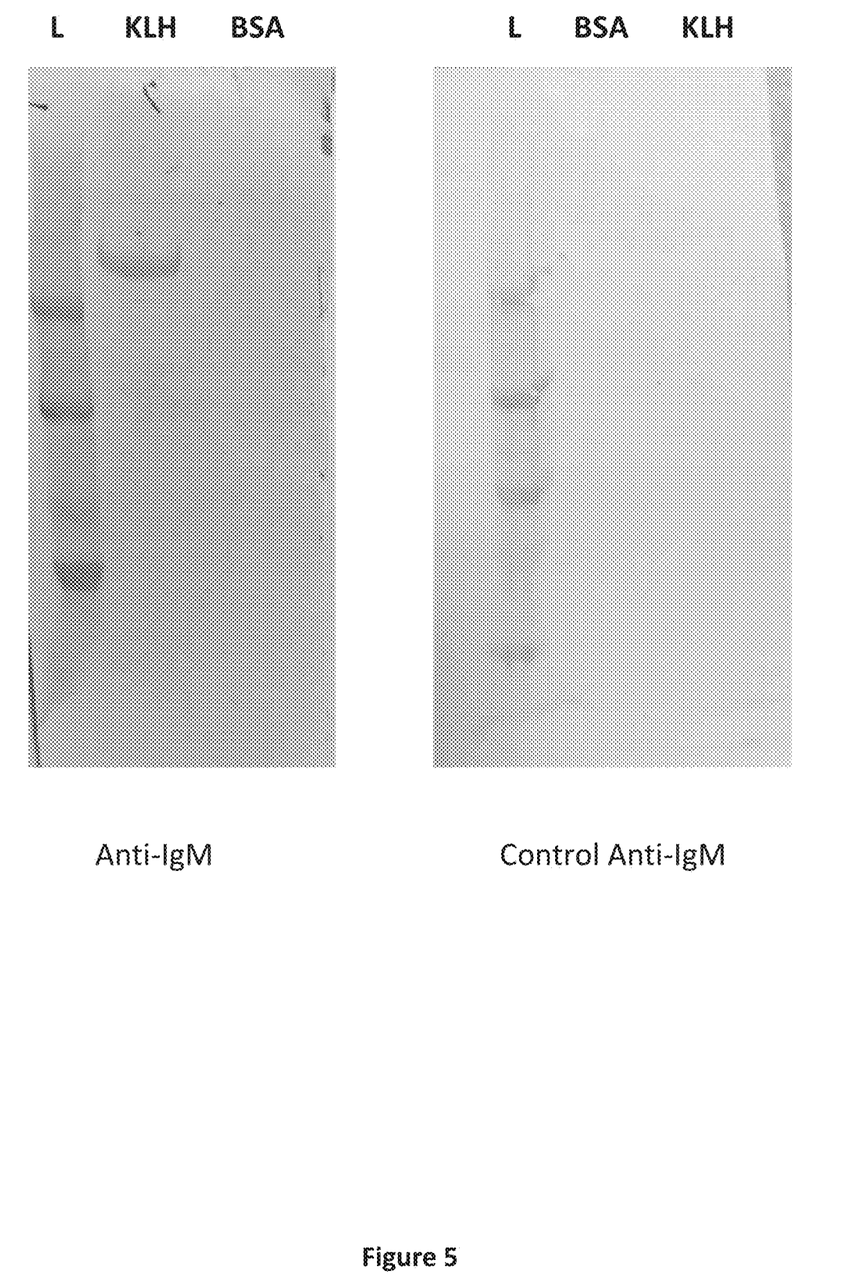
FIG. 5 illustrates the presence of IgM antibodies generated by zebrafish immunized against KLH, 2 months post-immunization, methods are the same as for FIG. 3, the PVDF membrane was incubated with whole fish homogenate from immunized (IgM) and non-immunized fish (control) (pool of 10 each) as described in the examples.
Figure 6:
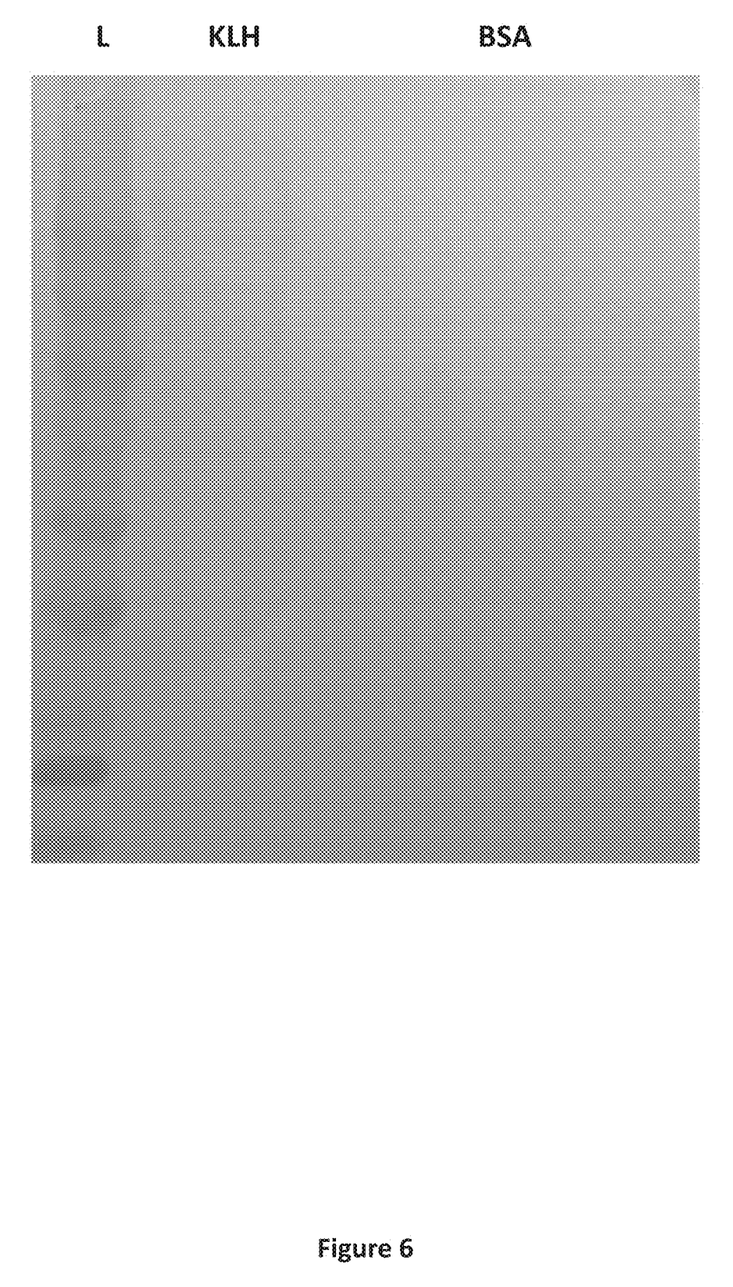
FIG. 6 illustrates the presence of IgM antibodies generated by zebrafish immunized against KLH, 4-months post-immunization KLH antigen and BSA were separated by 4 to 12% SDS-PAGE and transferred to a PVDF membrane, methods are the same as described in FIG. 3, lanes, L, Molecular weight markers; KLH; Keyhole Limpet Hemocyanin; BSA, bovine serum albumin control protein.
Figure 7:
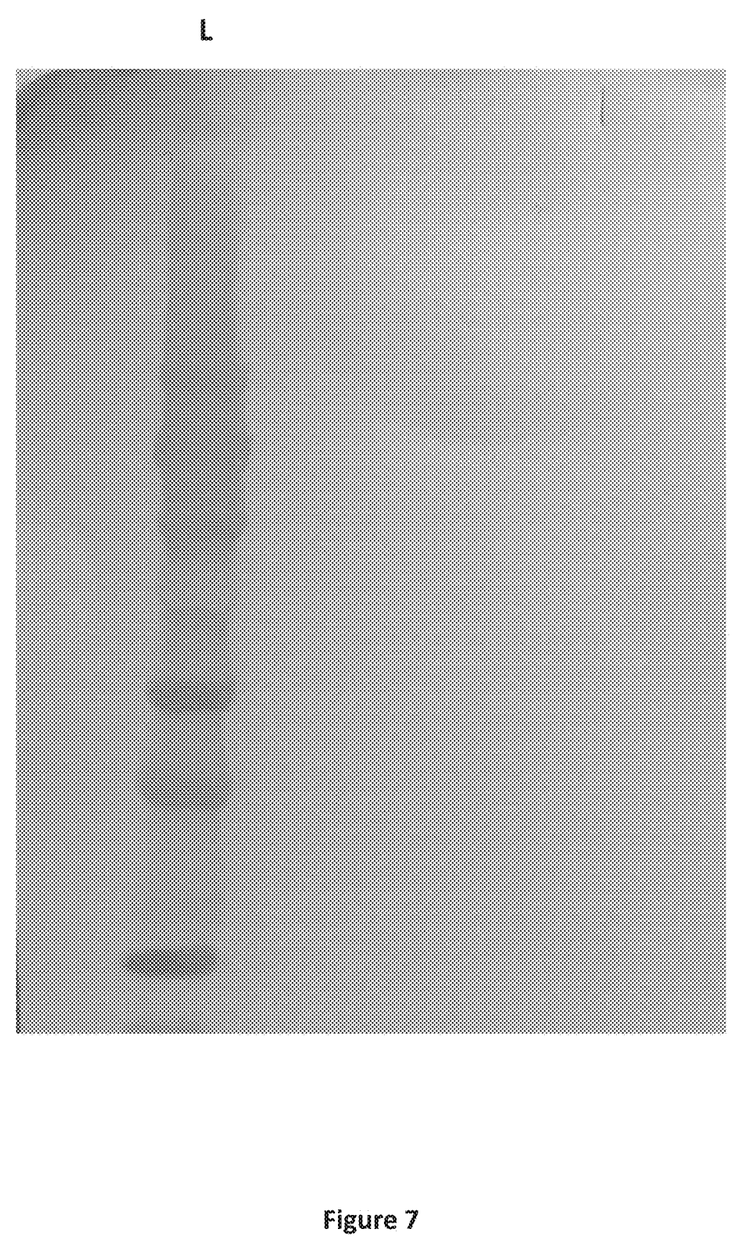
FIG. 7 illustrates the absence of IgM antibodies to KLH in non-immunized zebrafish 4 months post-injection, zebrafish were prepared as in FIG. 6, however, zebrafish were injected with carriers not associated with antigen, as in FIG. 6, antigen was separated by 4 to 12% SDS-PAGE and transferred to a PVDF membrane, lane, L, Molecular weight markers.

As evident from FIG. 3, zebrafish developed IgM directed against KLH by 1-month post-vaccination. No nonspecific binding was seen against BSA control protein. Similarly, as shown in FIG. 4, zebrafish produced both IgM and IgZ against *M. marinum* proteins, 1-month post-injection, when the method was used to immunize embryos against total *M. marinum* protein extract. As is further evident in FIG. 5, zebrafish continued to produce IgM directed against KLH at 2 months, and as further evident in FIG. 6, zebrafish still produced IgM directed against KLH at 4 months post vaccination, indicating the presence of an immune response against KLH antigen. FIG. 7 shows that zebrafish, injected with carriers not associated with any antigen, do not generate IgM on Western blots prepared with KLH antigen as in FIG. 6, at 4 months post injection.

The result of the inventor's research is that the inventor has found a way to effectively deliver protective or prophylactic therapeutic agents to fish embryos as a way to prevent and treat disease in fish utilizing injection into a fish embryo that is superior to other current therapeutic agent delivery methods. Once vaccinated, fish embryos effectively develop an immune response to the pathogen as they mature. The disclosed method is cost-effective, environmentally friendly, uses FDA approved carrier materials, is efficacious with a high margin of safety, and provides for closely controlled dosing.

SUMMARY OF THE INVENTION

The present disclosure reveals a method for the delivery of a therapeutic agent into a fish embryo in the one-cell to eyed egg stage of development.

To prevent disease-related morbidity and mortality by the method of injecting a therapeutic agent into fish embryos as early as 1-hour post fertilization, when the embryos are in the one-cell to the eyed egg stage of development, wherein the injection can be direct or with the use of microspheres as carriers of therapeutic agents. Once vaccinated or treated, fish embryos can effectively moderate their response to therapeutic agents as they mature. The most significant obstacle to effective prophylaxis or treatment of infectious diseases in early life stage fish is not the availability of vaccine agents and therapeutants, immunogenic potential or processing of the vaccine agent, but a method of delivery.

The inventor has developed method of therapeutically treating or vaccinating fish embryos as early as 1-hour post fertilization, when the embryos are in the one-cell to the eyed egg stage of development, by either directly injecting the therapeutic agent or antigen, or by utilizing injectable microspheres as a delivery platform to carry therapeutic agents or antigens, wherein the developed method is not only superior to other current therapeutic agent or vaccine delivery methods, but is effective for fish embryos. The disclosed method is cost-effective, environmentally friendly, uses FDA approved carrier materials, is efficacious with a high margin of safety, and provides for closely controlled dosing.

AMENDED DETAILED DESCRIPTION OF THE INVENTION

Figure 11:
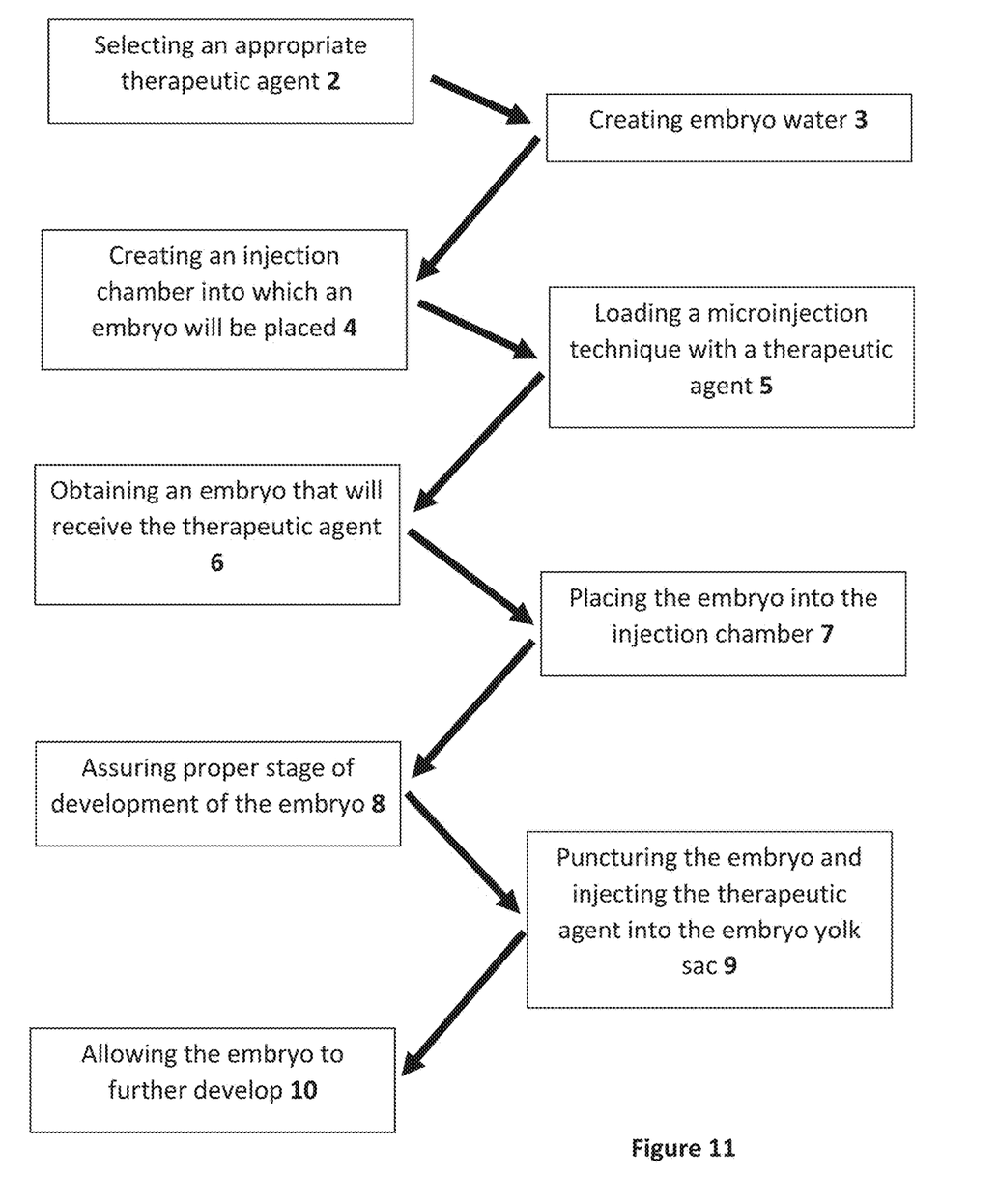
FIG. 11 illustrates the method of vaccination.
Figure 12:
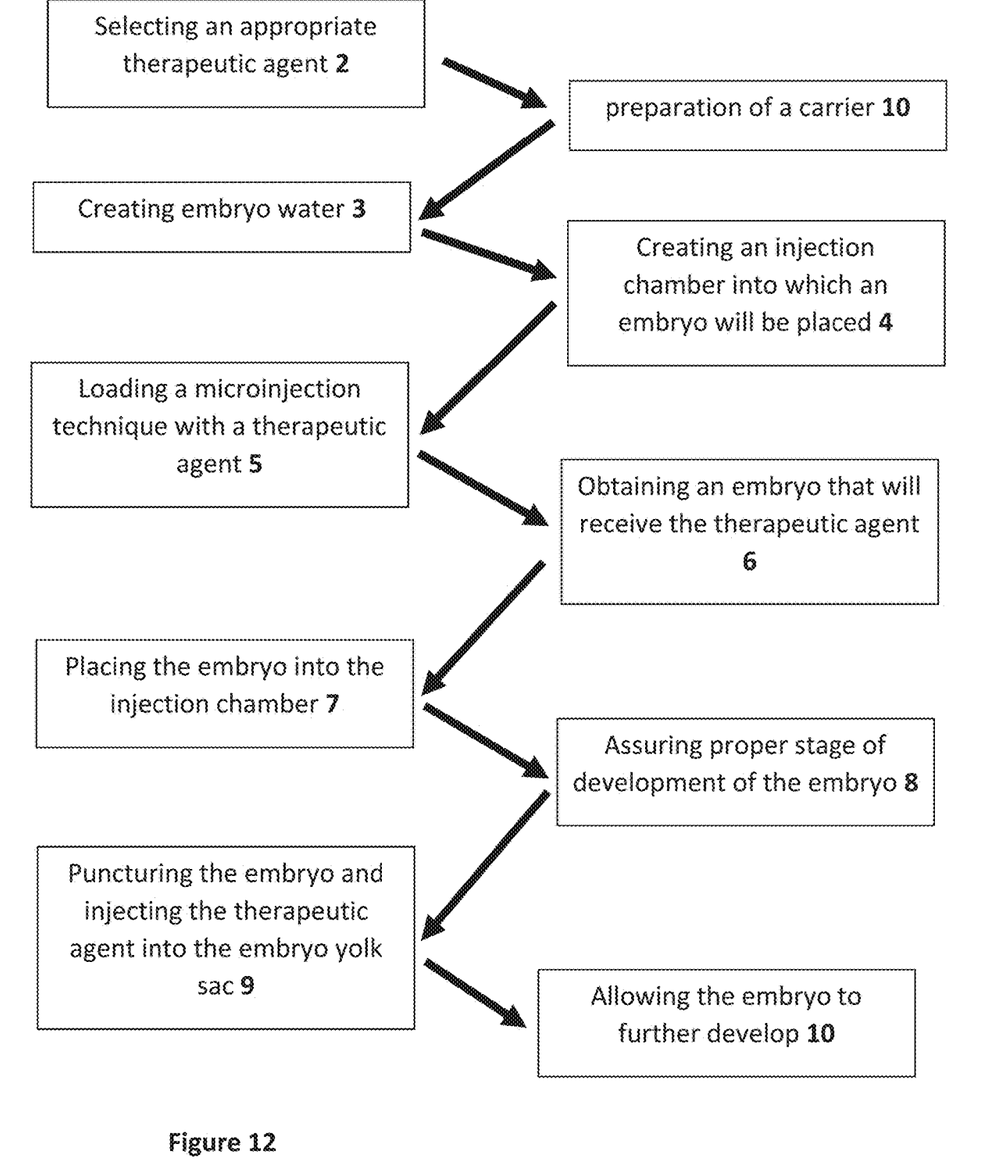
FIG. 12 illustrates the method of vaccination including the preparation of the microspheres used for vaccination.

The present disclosure reveals a method of vaccinating fish embryos with a therapeutic agent 1, wherein said vaccination takes place after fertilization and in particular within the one-cell to eyed egg stage of development comprising, not necessarily in sequential order, the following steps:

Selecting an appropriate therapeutic agent 2.

A therapeutic agent shall include at least one of all agents that may provide benefits to fish. By way of example and not by limitation, these include antibiotics (for example, keyhole limpet hemocyanin (KLH) or whole protein extract of *Mycobacterium marinum*), antifungals, antigens for immunization, pharmaceuticals, biologicals, and nutrients. Also included are agents which do not act directly to benefit fish but act in combination with other therapeutic agents, including immune system stimulants or adjuvants, which enhance an immune response in a host, after exposed to an antigen. Therapeutic agents including antigens may also be the products of genetic engineering. In addition to antigens, factors which act indirectly to enhance an immune response may also be associated with carriers. By way of example, M-cell homing peptide (amino acid sequence (CKSTHPLSC), may be associated with a carrier to create a specific targeting mechanism for larval and adult teleost fish. The term "Antibiotic" as used herein is meant to include but not be limited to florfenicol (Aquaflor® Type A and CA1), oxytetracycline (Terramycin® 200 for Fish (oxytetracycline dehydrate), Type A Medicated Article and OxyMarine™ oxytetracycline HCL Soluble Powder-343, Terramycin-343, TETROXY Aquatic), sulfamerazine, and sulfadimethoxine/ormetoprim combination (Romet-30®). Antifungal is meant to include but not be limited to triazole antifungals (fluconazole, itraconazole, voriconazole), allylamine antifungals (terbinafine), and amphotericin B. Biologicals include but not be limited to: peptides, nucleotides, nucleosides, antibodies, levamisole, interleukin-2, interleukin-7, interleukin-9, siRNA and DNA, melittin, and nutraceutical class therapeutics. Nutrients is meant to include but not be limited to L-lysine, L-arginine, xanthophyll, chitosan, glucosamine, plant proteins, micronutrients (vitamins and minerals), probiotics, and essential and non-essential amino acids including Taurine.

Obtaining embryo water 3.

Embryo water is derived from available source water or a combination of reverse osmosis (RO) water and available synthetic sea salt mixture to a salinity of 100 to 60,000 ppm and is specific to the type of embryo that will receive the injection.

Obtaining an injection chamber, into which an embryo will be placed 4 to immobilize the embryo, wherein said injection chamber is designed to hold a fish egg specific to the type of fish to be injected, from the size of a flying fish (Tobiko) fish egg to a whale shark fish egg.

During this step, it is possible to create an injection chamber, by way of example but not limited to, a first layer of gel created and allowed to solidify, followed by the application of a second layer of gel and a mold placed in the liquid so that once the mold is removed an injection chamber is created. Said gel is created from a substance such as but not limited to agarose. Once the injection chamber is created the injection chamber is filled with embryo water.

Loading an injection technique with a therapeutic agent 5.

Any method of injection, including fully automated or with speed trajectory optimization of the micropipette injection motion may be utilized in the present invention provided it is able to inject the therapeutic agent or a solution containing carriers by way of example PLGA beads, into the yolk sac of a fish embryo without compromising vital structures (Chen P. C. Y., Zhou. S., Lu Z. et al. Int. J. Control Autom. Syst. (2015) 13: 1233; Spaink H. P., Cui C., Wiweger M. I. et al. Methods (2013) 62(3): 246-254; Wang W, Liu X, Gelinas D, Ciruna B, Sun Y (2007) PLoS ONE 2(9): e862). The injection technique is filled with the therapeutic agent, wherein the injection technique shall further comprise a needle having a diameter of 0.1 to 6000 microns.

Obtaining an embryo that will receive the therapeutic agent 6.

A newly spawned embryo is selected for vaccination, most preferably within one hour of fertilization, wherein the embryo is in the one-cell to eyed egg stage of development.

Placing the embryo into the injection chamber 7.

Assuring proper stage of development of the embryo 8.

The assessing the stage of development and the monitoring of the injection process is observable visually or microscopically, wherein the magnification of the microscope is typically between 10× and 1000× magnification. Ideally, embryos are injected while in the single cell stage of development. However, fish embryos may be vaccinated, as long as injection is possible without injury to vital developing anatomical structures. By way of non-limiting example, immunizing zebrafish embryos that have exceeded 4 hours post-fertilization is preferably avoided.

Puncturing the embryo with the needle to inject the therapeutic agent into the embryo yolk sac 9.

The embryo comprises a membrane, and yolk sac. Insertion of the needle into an embryo is performed with the use of micromanipulators while the process is monitored microscopically. Injection of a volume of therapeutic agent, non-destructively, is accomplished, by inserting the needle through a membrane and into the yolk sac, and applying pressure to the therapeutic agent in the needle to inject the volume, after which the needle is withdrawn. Effective amounts of therapeutic agent to be injected are expected to vary depending on the therapeutic agent and species of fish.

Allowing the embryo to further develop 10.

The injected embryos may subsequently be allowed to develop in any suitable environment. Although it is envisioned that this procedure will typically take place at an aquaculture facility such as a fish hatchery, where injected embryos will be returned to controlled conditions for continued development, no such limitation is placed on the further treatment or development of the injected embryos.

The disclosure may also comprise an additional step that involves the preparation of a carrier 10.

A carrier is microsphere combined with a therapeutic agent. A microsphere can be but is not necessarily limited to conventional normal phase polymeric micelles, liposomes, empty core nanoparticles, solid nanoparticles, latex beads, gold beads, aluminum beads, alginate, microspheres, β-glucan, chitin, Polylactic-co-glycolic acid (PLGA), Polylactic acid (PLA), and Polycaprolactone (PCL) as well as other natural and synthetic biopolymers. The microsphere is combined with the therapeutic agent by at least one of coating, incorporation, binding, uptake by, absorption by, or adhering to a microsphere, including the use of linking agents that may aid in the association of either therapeutic agents or components. In some instances covalent attachment, for example, the use of polylactic-co-glycolic (PLGA) microspheres, may be useful with some carriers. For example, covalent attachment of biomolecules using water soluble carbodiimides is described by Hoffman et al., "Covalent Binding of Biomolecules to Radiation-Grafted Hydrogels on Inert Polymer Surfaces," Trans. Am. Soc. Artif. Intern. Organs, 18, 10-18 (1972); and Ito et al., "Materials for Enhancing Cell Adhesion by Immobilization of Cell-Adhesive Peptide," J. of Biomed. Mat. Res., 25, 1325-1337 (1991). The carrier is in a solution and it is that solution with carrier that is injected into the fish.

What is claimed:

1. A method of immunizing a fish embryo post fertilization, when the embryo is in the one-cell to the eyed egg stage state of development, wherein the method comprises:

selecting a therapeutic agent, said therapeutic agent to include at least one of keyhole limpet hemocyanin (KLH) or whole protein extract of *Mycobacterium marinum;* obtaining embryo water wherein said embryo water comprises water or reverse osmosis (RO) water and wherein the embryo water comprises a salinity of 100 to 60,000 ppm;

obtaining an injection chamber, wherein said injection chamber is designed to immobilize an embryo specific to the type of fish to be injected, from the size of a flying fish embryo to a whale shark embryo;

filling the injection chamber with embryo water;

loading a means of injection comprising a needle for injection with the therapeutic agent, said needle having a diameter of 0.1 to 6000 microns;

obtaining a fish embryo that will receive the therapeutic agent, said fish embryo to be a zebrafish embryo;

placing the fish embryo into the injection chamber;

assuring proper stage of development of the fish embryo, wherein embryo is comprised of a plurality of cells, the stage of development is dependent upon the number of cells within the fish embryo, and the stage of development is identified visually or with the use of a microscope wherein the microscope has a magnification between 10× and 1000×;

puncturing the fish embryo with the needle to inject the therapeutic agent, wherein the fish embryo comprises a membrane and a yolk sac, and the needle punctures the membrane and the therapeutic agent is injected into the yolk sac; and allowing the embryo to further develop.

2. The method of claim 1 wherein the injection chamber is created by placing a first layer of gel, followed by the application of a second layer of gel and the insertion of a mold into the second layer of gel, so that once the mold is removed the injection chamber is created.

3. The method of claim 1 wherein the stage of development of the fish embryo is at one-cell to eyed egg stage.

4. The method of claim 3 wherein the injection chamber is created by placing a first layer of gel, followed by the application of a second layer of gel and the insertion of a mold into the second layer of gel, so that once the mold is removed the injection chamber is created.

5. A method of immunizing a fish embryo post fertilization, when the embryo is in the one-cell to the eyed egg stage state of development, wherein the method comprises:

selecting a therapeutic agent, said therapeutic agent to include at least one of keyhole limpet hemocyanin (KLH) or whole protein extract of *Mycobacterium marinum;* preparing a carrier, wherein a carrier comprises a microsphere combined with the therapeutic agent, said microsphere to be selected from at least one of a conventional normal phase polymeric micelles, liposomes, empty core nanoparticles, solid nanoparticles, latex beads, gold beads, aluminum beads, alginate, microspheres, β-glucan, chitin, Polylactic-co-glycolic acid (PLGA), Polylactic acid (PLA), and/or Polycaprolactone, wherein the microsphere is combined with the therapeutic agent by at least one of coating, incorporation, binding, uptake by, absorption by, and/or adhering to a microsphere;

obtaining embryo water wherein said embryo water comprises water or reverse osmosis (RO) water and wherein the embryo water comprises a salinity of 100 to 60,000 ppm;

obtaining an injection chamber, wherein said injection chamber is designed to immobilize an embryo specific to the type of fish to be injected, from the size of a flying fish embryo to a whale shark embryo;

filling the injection chamber with embryo water;

loading a means of injection comprising a needle for injection with the therapeutic agent, said needle having a diameter of 0.1 to 6000 microns;

obtaining a fish embryo that will receive the therapeutic agent, said fish embryo to be a zebrafish embryo;

placing the fish embryo into the injection chamber;

assuring proper stage of development of the fish embryo, wherein embryo is comprised of a plurality of cells, the stage of development is dependent upon the number of cells within the fish embryo, and the stage of development is identified visually or with the use of a microscope wherein the microscope has a magnification between 10× and 1000×;

puncturing the fish embryo with the needle to inject the therapeutic agent, wherein the fish embryo comprises a membrane and a yolk sac, and the needle punctures the membrane and the therapeutic agent is injected into the yolk sac; and allowing the embryo to further develop.

6. The method of claim 5 wherein the injection chamber is created by placing a first layer of gel, followed by the application of a second layer of gel and the insertion of a mold into the second layer of gel, so that once the mold is removed the injection chamber is created.

7. The method of claim 5 wherein the stage of development of the fish embryo is at one-cell to eyed egg stage.

8. The method of claim 7 wherein the injection chamber is created by placing a first layer of gel, followed by the application of a second layer of gel and the insertion of a mold into the second layer of gel, so that once the mold is removed the injection chamber is created.

9. The method of claim 5 wherein, in the preparation of the carrier a covalent attachment, polylactic-co-glycolic (PLGA) microspheres, is used to facilitate the combination of the micro sphere with the therapeutic agent.

10. The method of claim 9 wherein the injection chamber is created by placing a first layer of gel, followed by the application of a second layer of gel and the insertion of a mold into the second layer of gel, so that once the mold is removed the injection chamber is created.

11. The method of claim 9 wherein the stage of development of the fish embryo is at one-cell to eyed egg stage.

12. The method of claim 11 wherein the injection chamber is created by placing a first layer of gel, followed by the application of a second layer of gel and the insertion of a mold into the second layer of gel, so that once the mold is removed the injection chamber is created.

13. The method of claim 2 wherein the stage of development of the fish embryo is at one-cell to eyed egg stage.

14. The method of claim 13 wherein the injection chamber is created by placing a first layer of gel, followed by the application of a second layer of gel and the insertion of a mold into the second layer of gel, so that once the mold is removed the injection chamber is created.

* * * * *